United States Patent [19]

Nakao et al.

[11] Patent Number: 5,597,918
[45] Date of Patent: Jan. 28, 1997

[54] FUSED PYRIDAZINE COMPOUND

[75] Inventors: Tohru Nakao; Hiroshi Tanaka, both of Fukuoka; Yasuto Morimoto, Osaka; Shuzo Takehara, Fukuoka, all of Japan

[73] Assignee: Yoshitomi Pharmaceutical Industries, Ltd., Osaka, Japan

[21] Appl. No.: 460,758

[22] Filed: Jun. 2, 1995

Related U.S. Application Data

[63] Continuation of Ser. No. 208,950, Feb. 28, 1994, abandoned.

[30] Foreign Application Priority Data

Aug. 27, 1991 [JP] Japan ..................... 3-240378

[51] Int. Cl.$^6$ ................................ C07D 495/04
[52] U.S. Cl. ................ 544/234; 549/51; 549/57
[58] Field of Search ........................... 544/234

[56] References Cited

U.S. PATENT DOCUMENTS

| | | | |
|---|---|---|---|
| 4,849,421 | 7/1989 | Nakao et al. | 514/248 |
| 4,965,264 | 10/1990 | Nakao et al. | 514/248 |
| 5,153,194 | 10/1992 | Nakao et al. | 514/248 |
| 5,175,162 | 12/1992 | Nakao et al. | 544/234 |

FOREIGN PATENT DOCUMENTS

| | | |
|---|---|---|
| 0190367 | 8/1986 | European Pat. Off. . |
| 0426018 | 5/1991 | European Pat. Off. . |
| 64-6278 | 1/1989 | Japan . |
| 1-250383 | 10/1989 | Japan . |
| 2-69481 | 3/1990 | Japan . |
| 2-167285 | 6/1990 | Japan . |

OTHER PUBLICATIONS

I. Nakao et al, "Studies on the Synthesis of Condensed Pyridazine Derivatives. IV. Synthesis and Anxiolytic Activity of 2–Aryl–5,6–dihydro–(1)benzothiepino[5,4–c]pyridazin–3(2H)–ones and Related Compound" *Chem. Pharm. Bull.* 39(10) 2556–2563 (1991).

*Primary Examiner*—Emily Bernhardt
*Attorney, Agent, or Firm*—Sughrue, Mion, Zinn, Macpeak & Seas

[57] ABSTRACT

A fused pyridazine compound of the formula $$\text{(I)}$$

wherein each symbol is as defined in the description.

The compounds of the present invention are useful as anxiolytic agents which selectively act on anxiety because of having less side effects (e.g. muscle-relaxation, sedation or interaction with alcohol/barbiturates).

4 Claims, No Drawings

FUSED PYRIDAZINE COMPOUND

CROSS-REFERENCE TO RELATED APPLICATIONS

This is a continuation of application of 08/208,950, filed Feb. 28, 1994 (abandoned), which is a continuation-in-part application of International Application No. PCT/JP92/01067 filed Aug. 24, 1992.

FIELD OF THE INVENTION

The present invention relates to fused pyridazine compounds useful as anxioselective anxiolytic agents.

BACKGROUND OF THE INVENTION

Benzodiazepine (BZP) derivatives represented by diazepam have been used as, for example, anxiolytic agents. BZP agents exhibit excellent anxiolytic activity in human beings, whereas they are known to cause undesirable adverse reactions (side effects) such as sedation, muscle-relaxation and interaction with alcohol/barbiturates. Therefore, the development of anxioselective anxiolytic agents with less side effects than conventional BZP derivatives has been desired.

On the other hand, it has been proved that receptors which have specific affinity for BZP derivatives exist in the central nervous system by a late pharmacological study [Science, vol. 198, 848 (1977)]. The findings of BZP receptors in the central nervous system have remarkably advanced the research on the mechanism of BZP agents. It was suggested that the BZP receptor forms a complex with the γ-aminobutyric acid (GABA) receptor and the Cl⁻ ionophore, and BZPs exhibit pharmacological activity through the GABA response. That is, the compounds which act on the BZP receptors can be classified with different efficacy on a continuum from full agonists to inverse agonists, according to their modulatory effects on GABAergic transmission. Furthermore, they are classified into full agonists, partial agonists, antagonists, partial inverse agonists and inverse agonists in consideration of their behavioral pharmacological properties.

Recently, research works have emphasized the search for anxiolytic agents which selectively act on anxiety and have less side effects such as sedation, muscle-relaxation, potentiation of alcoholic effect or dependency liability associated with BZP agents. In the process of these investigations, many compounds have been found which possess high affinity for BZP receptors in spite of their different structures from BZP (U.S. Pat. No. 4,849,421, U.S. Pat. No. 4,965,264 and U.S. Pat. No. 5,153,194). Among them, the compounds classified into BZP partial agonists have become important as a new type of anxiolytic agents since they are dissociated from side effects but exhibit selective pharmacological activity against anxiety.

SUMMARY OF THE INVENTION

The present inventors have conducted intensive investigations in order to develop anxiolytic agents having non-BZP structures and selective anxiolytic activity with high safety, and have found novel fused pyridazine compounds in which displayed anxioselective anxiolytic activity with less side effects because of not only high affinity for BZP receptors but also BZP partial agonistic property.

DETAILED DESCRIPTION

That is, the present invention provides:
1. a fused pyridazine compound of the formula:

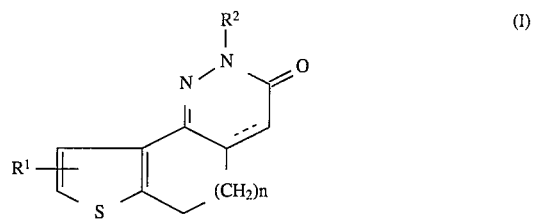

wherein:
R¹ is alkanoyl having 2 to 5 carbon atoms, hydroxyalkyl having 1 to 4 carbon atoms in the alkyl moiety, or alkoxyalkyl having 1 to 4 carbon atoms in the each of alkoxy and alkyl moieties;
R² is phenyl having at least one substituent selected from the group consisting of halogen, alkyl having 1 to 4 carbon atoms and alkoxy having 1 to 4 carbon atoms, or heteroaryl;
n is 1 or 2;
the bond represented by full line and dotted line is a single bond or a double bond;

2. a fused pyridazine compound according to item 1, wherein R¹ is alkanoyl having 2 to 5 carbon atoms, hydroxyalkyl having 1 to 4 carbon atoms in the alkyl moiety, or alkoxyalkyl having 1 to 4 carbon atoms in the each of alkoxy and alkyl moieties; R² is phenyl having 1 to 3 substituents selected from the group consisting of halogen, alkyl having 1 to 4 carbon atoms and alkoxy having 1 to 4 carbon atoms, or pyridyl; n is 1 or 2; and the bond represented by full line and dotted line is a single bond or a double bond;

3. a fused pyridazine compound according to item 1, wherein R¹ is alkanoyl having 2 to 5 carbon atoms, hydroxyalkyl having 1 to 4 carbon atoms in the alkyl moiety, or alkoxyalkyl having 1 to 4 carbon atoms in the each of alkoxy and alkyl moieties; R² is phenyl having 1 to 3 substituents selected from the group consisting of halogen, alkyl having 1 to 4 carbon atoms and alkoxy having 1 to 4 carbon atoms; n is 1 or 2; and the bond represented by full line and dotted line is a single bond or a double bond;

4. a fused pyridazine compound according to item 1, which is selected from the group consisting of:
9-methoxymethyl-2-(4-methylphenyl)-2,5,6,7-tetrahydro-3H-thieno-[2',3':6,7]cyclohepta[1,2-c]pyridazin-3-one,
9-acetyl-2-(4-chlorophenyl)-2,4,4a, 5,6,7-hexahydro-3H-thieno-[2',3':6,7]cyclohepta[1,2-c]pyridazin-3-one, and
8-(1-hydroxyethyl)-5,6-dihydro-2-(4-methylphenyl)thieno-[2,3-h]-cinnolin-3(2H)-one;

5. a fused pyridazine compound according to item 1, which is 9-methoxymethyl-2-(4-methylphenyl)-2,5,6,7-tetrahydro-3H-thieno-[2',3':6,7]cyclohepta[1,2-c]pyridazin-3-one;

6. a fused pyridazine compound according to item 1, which is 9-acetyl-2-(4-chlorophenyl)-2,4,4a, 5,6,7-hexahydro-3H-thieno-[2',3':6,7]cyclohepta[1,2-c]pyridazin-3-one; and 7. a fused pyridazine compound according to item 1, which is 8-(1-hydroxyethyl)-5,6-dihydro-2-(4-methylphenyl)thieno-[2,3-h ]cinnolin-3(2H)one.

With regard to the above-mentioned formula (I), in the R¹, the term alkanoyl having 2 to 5 carbon atoms means acetyl, propionyl, butyryl, isobutyryl, pentanoyl or pivaloyl, preferably acetyl or propionyl, and more preferably acetyl. The term hydroxyalkyl having 1 to 4 carbon atoms in the alkyl moiety means hydroxymethyl, 1- or 2-hydroxyethyl, 1-, 2- or 3-hydroxypropyl or 1-, 2-, 3- or 4-hydroxybutyl, preferably hydroxymethyl or 1-hydroxyethyl, and more preferably 1-hydroxyethyl. The term alkoxyalkyl having 1 to 4 carbon atoms in the each of alkoxy and alkyl moieties means methoxymethyl, 1- or 2-methoxyethyl, 1-, 2- or 3-methoxypropyl, 1-, 2-, 3- or 4-methoxybutyl, ethoxymethyl, 1- or 2-ethoxyethyl, 1-, 2- or 3-ethoxypropyl or 1-, 2-, 3- or 4-ethoxybutyl, preferably methoxymethyl, ethoxymethyl or 2-methoxyethyl, and more preferably methoxymethyl.

In the $R^2$, the term heteroaryl means pyridyl, thienyl or furyl, preferably pyridyl. In the phenyl having at least one substituent selected from the group consisting of halogen, alkyl having 1 to 4 carbon atoms and alkoxy having 1 to 4 carbon atoms, the term halogen means chlorine, bromine, fluorine or iodine, preferably chlorine, the term alkyl having 1 to 4 carbon atoms means methyl, ethyl, propyl, isopropyl, butyl, isobutyl, sec-butyl or tert-butyl, preferably methyl, and the term alkoxy having 1 to 4 carbon atoms means methoxy, ethoxy, propoxy, isopropoxy, butoxy, isobutoxy, sec-butoxy or tert-butoxy, preferably methoxy. The number of the substituent is preferably 1 to 3 and more preferably 1.

Preferable examples of $R^1$ are acetyl, 1-hydroxyethyl and methoxymethyl, and preferable examples of $R^2$ are 4-chlorophenyl, 4-methylphenyl and 4-methoxyphenyl.

Preferable compounds of the formula (I) are 9-methoxymethyl-2-(4-methylphenyl)-2,5,6,7-tetrahydro-3H-thieno-[2', 3':6,7]cyclohepta[1,2-c]pyridazin -3-one, 9-acetyl-2-(4-chlorophenyl)-2,4,4a, 5,6,7-hexahydro-3H-thieno[2',3':6,7]cyclohepta[1,2-c]pyridazin-3-one and 8-(1-hydroxyethyl)-5,6-dihydro-2o (4-methylphenyl)thieno-[2,3-h ]cinnolin-3(2H)-one.

The compound of formula (I) having a chiral atom can be prepared as a racemate or an optically active isomer, and the compound having at least two chiral atoms can be obtained as an individual diastereomer or a mixture thereof. The present invention embraces the mixture thereof and the individual isomers. Furthermore, the present invention embraces stereoisomers.

The compounds of the present invention can be prepared by the following methods.

Method (1)

A compound of the formula

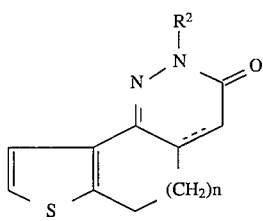 (1)

wherein each symbol is as defined above, is reacted with a carboxylic acid of the formula $R^3COOH$ (2)

wherein $R^3$ is alkyl having 1 to 4 carbon atoms or haloalkyl, or a reactive derivative thereof (e.g. acid halide, acid anhydride, mixed acid anhydride or ester) to produce a compound of the formula

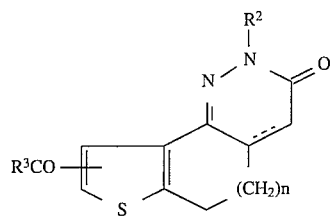 (3)

wherein each symbol is as defined above.

In the case where a free carboxylic acid compound of the formula (2) is employed, the reaction is conducted in the presence of a dehydrating agent (e.g. polyphosphoric acid) at room temperature to 150° C.

In the case where an acid halide (e.g. acid chloride, acid bromide or acid iodide) as the reactive derivative of the formula (2) is employed, the reaction is conducted in the presence of Lewis acid (e.g. aluminum chloride, tin chloride or iron chloride) in a suitable inert solvent (e.g. benzene, toluene, chloroform, methylene chloride or dichloroethane) at −10° C. to 100° C. for 5 minutes to 20 hours.

Method (2)

The compound obtained in the Method (1) is subjected to a chemical reduction with a reducing agent such as sodium borohydride, lithium aluminum hydride or triethylsilane in a suitable inert solvent (e.g. methanol, ethanol, propanol, butanol or acetic acid), or a catalytic reduction in the presence of palladium, rhodium or platinum at −10° C. to 150° C. for 5 minutes to 20 hours to produce the compound of formula (I) wherein $R^1$ is 1-hydroxyalkyl and so on. The resulting compound is represented by the formula

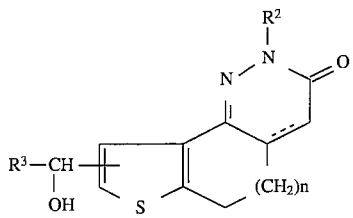 (4)

wherein each symbol is as defined above.

Method (3)

The compound of formula (1) is subjected to the Vilsmeier-Haack reaction to produce a compound of the formula

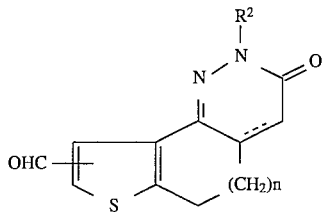 (5)

wherein each symbol is as defined above.

The reaction is carried out by reacting the compound of formula (I) with a formylation agent (e.g. N, N-dimethylformamide or N-methylformanilide) in the presence of phosphorus oxychloride at 0° C. to 100° C. for 10 minutes to 10 hours.

Method (4)

The compound of formula (5) is reduced by a reducing agent (e.g. sodium borohydride, sodium cyanoborohydride or lithium aluminum hydride) in an inert solvent (e.g. methanol, ethanol, propanol, butanol or tetrahydrofuran) at −10° C. to 50° C. for 5 minutes to 3 hours to produce a compound of the formula

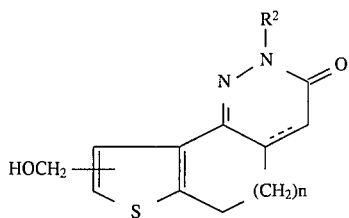

wherein each symbol is as defined above,
Method (5)

The haloalkanoyl compound obtained in the Method (1) represented by the formula

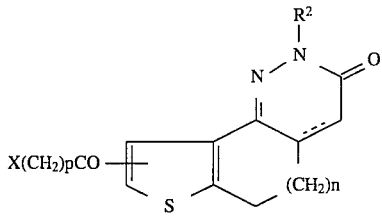

wherein p is 1 to 3, X is halogen and other symbols are as defined above, is reacted with a metal salt (e.g sodium salt, potassium salt or lithium salt) of a carboxylic acid compound of the formula $$R^5COOH \qquad (7)$$

wherein $R^5$ is alkyl having 1 to 4 carbon atoms.

The reaction is carried out in a suitable inert solvent (e.g. acetic acid, chloroform, methylene chloride, benzene, toluene or N, N-dimethylformamide) at room temperature to 150° C. for 1 to 20 hours to produce a compound of the formula

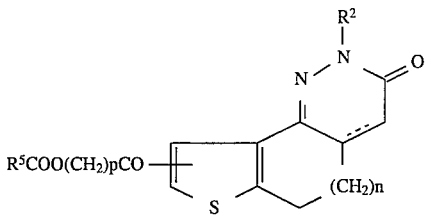

wherein each symbol is as defined above.

Further, the compound of formula (8) is reduced in a similar manner as in the Method (2) to produce a compound of the formula

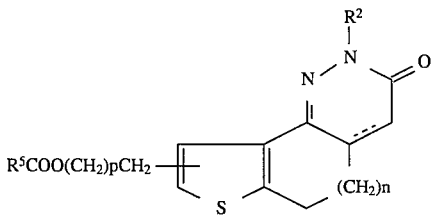

wherein each symbol is as defined above.
Method (6)

The compound of the formula (9) is reacted with an aqueous solution of an acid (e.g. hydrochloric acid, sulfuric acid, phosphoric acid or nitric acid) or an alkali (e.g. sodium hydroxide, potassium hydroxide, lithium hydroxide, barium hydroxide or potassium carbonate) in a suitable inert solvent (e.g. acetic acid, methanol, ethanol, butanol or water) at −10° C. to 150° C. for 1 to 20 hours to produce a compound of the formula

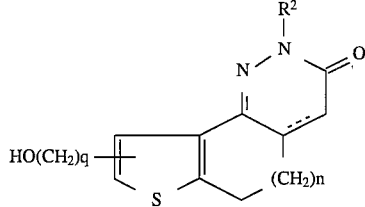

wherein each symbol is as defined above.
Method (7)

A compound obtained in the Method (4) and Method (6) represented by the formula

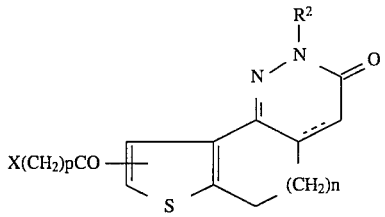

wherein q is 1, 2,3 or 4 and other symbols are as defined above, is reacted with a compound of the formula $$R^6X \qquad (12)$$

wherein $R^6$ is alkyl having 1 to 4 carbon atoms and X is as defined above, in a suitable inert solvent (e.g. methanol, ethanol, propanol, butanol, N, N-dimethylformamide, tetrahydrofuran, benzene or toluene) in the presence of an acid scavenger (e.g. sodium hydride, sodium amide, sodium methoxide, sodium ethoxide, potassium hydroxide or sodium hydroxide) at room temperature to the boiling point of the solvent employed for 1 to 20 hours to produce a compound of the formula

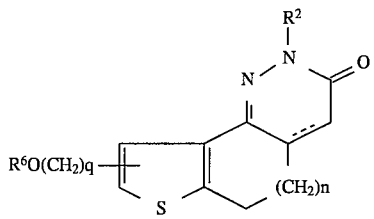

wherein each symbol is as defined above.
Method (8)

The compound of formula (13) can also be produced by reacting a compound of the formula (11) with a compound of the formula $$R^6OH \qquad (14)$$

wherein $R^6$ is as defined above, in a suitable inert solvent (e.g. benzene, toluene, tetrahydrofuran, chloroform or methylene chloride) or without solvent in the presence of a suitable acidic catalyst (e.g. hydrochloric acid, sulfuric acid, nitric acid or p-toluenesulfonic acid) at room temperature to 100° C. for 30 minutes to 24 hours.
Method (9)

The compound of formula (I) wherein $R^1$ is 1-alkoxyalkyl can be produced by conducting a reaction in a similar manner as in the Method (7) or Method (8) using a compound of the formula (4) obtained in the Method (2).
Method (10)

The compound of formula (I) wherein the bond represented by full line and dotted line is a double bond can also be prepared by adding bromine dropwise in an amount of 1 to 1.5 times mol to the corresponding compound of the formula (I) wherein the bond represented by full line and dotted line is a single bond in an acetic acid as the solvent at 20° C. to 60° C. [Journal of Medicinal Chemistry, vol. 14, 262 (1971)] or by reacting the compound of formula (I) wherein the bond represented by full line and dotted line is a single bond with sodium-m-nitrobenzenesulfonate (Bachmann method, the specification of United Kingdom Patent No. 1168291).

The thus obtained compounds of the present invention can be isolated and purified by a conventional method such as recrystallization or column chromatography.

When the obtained compound is a racemate, it can be separated into desired optically active isomers by means of, for example, fractional recrystallization of a salt with an optically active acid or column chromatography filled with an optically active carrier. The individual diastereomers can be separated by the method such as fractional crystallization or chromatography. Such compounds can also be obtained by using an optically active starting material. Furthermore, the stereoisomers can be isolated by, for example, recrystallization or column chromatography.

Among the compounds of formula (1) which are starting materials, the compound wherein the bond represented by full line and dotted line is a single bond, that is, the compound of formula

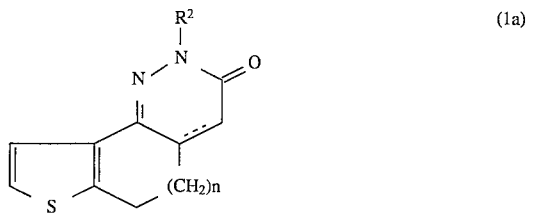

(1a)

wherein each symbol is as defined above, can be prepared by reacting a compound of the formula

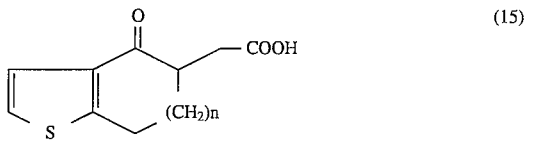

(15)

wherein n is as defined above, with a hydrazine derivative of the formula $R^2$—$NHNH_2$ (16)

wherein $R^2$ is as defined above, or an acid addition salt thereof, and then subjecting the thus obtained compound of formula

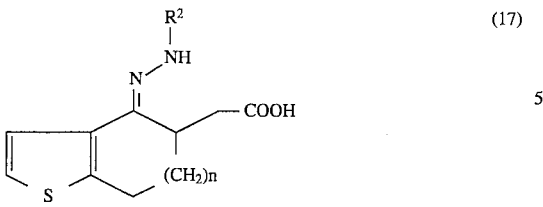

(17)

wherein each symbol is as defined above, to a ring closure reaction.

The reaction is carried out by refluxing the mixture of the compound of formula (15) and the compound of formula (16) under heating for 5 to 20 hours in a suitable inert solvent (e.g. alcohol such as methanol, ethanol or propanol, or benzene, toluene) to produce the compounds of formula (1a) and (17).

In the case where the hydrazine derivative of formula (16) is an acid addition salt thereof, the reaction is carried out in the presence of an acid scavenger (e.g. sodium acetate, potassium acetate, sodium hydrogen carbonate, sodium carbonate, potassium carbonate, pyridine or triethylamine).

In the case where the compound of formula (17) is obtained, the compound of formula (1a) can be prepared by refluxing the compound of formula (17) under heating for 5 to 10 hours in acetic acid.

Further, the compound of formula (1) wherein the bond represented by full line and dotted line is a double bond, that is, the compound of formula

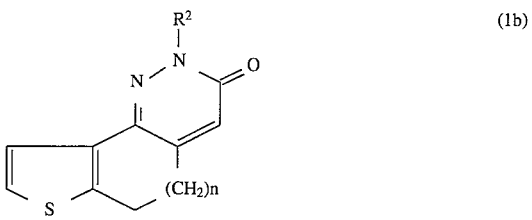

(1b)

wherein each symbol is as defined above, can be prepared by oxidizing the compound of formula (1a).

The reaction is carried out in a suitable acidic solvent (e.g. acetic acid, trifluoroacetic acid or methanesulfonic acid) in the presence of a suitable sulfoxide (e.g. dimethyl sulfoxide, diphenyl sulfoxide or methyl phenyl sulfoxide) with or without a suitable acid (e.g. hydrogen halides such as hydrogen bromide) at 0° C. to near the boiling point of the solvent employed to produce the compound of formula (1b).

Experiment 1: Displacement ability for benzodiazepine receptor

The test of specific binding to benzodiazepine (BZP) receptors was carried out according to the method described in Life Science, vol. 20, 2101 (1977).

The crude synaptosome fraction isolated from the cerebral cortex of male Wistar rats aged 9–10 weeks, was suspended in 50 mM Tris-hydrochloric acid buffer (pH 7.4) containing 120 mM sodium chloride and 5 mM potassium chloride. The suspension was used for the following experiment.

The test compound in several different concentrations and tritiated diazepam (in final concentration of 2 nM) were added to the synaptosomal suspension, and the mixture was incubated at 0° C. for 20 minutes. The suspension was filtered with Whatman GF/B (Trademark) glassfiber filter. After the filter was washed with the above-mentioned buffer, the radio activity left on the filter was measured with a liquid scintillation counter.

The specific binding was determined by subtracting the binding in the presence of $10^{-6}$M unlabelled diazepam from total binding.

The affinity for benzodiazepine receptors of the compound of the present invention is evaluated from its displacement ability for tritiated diazepam at its binding site, which is represented by Ki value (nM). The results were shown in Table 1.

Experiment 2: Effects on GABA-induced chloride current (concentration-clamp method)

The test was carried out according to the method of Akaike et al. reported in Journal of Physiology (London), 379, 171 (1986) using sensory neurons isolated from dosal root ganglion of American bullfrogs. Neurons were voltage-clamped at a holding membrane potential of −50 mV with a single-electrode voltage-clamp system. Test compounds were applied by using a concentration-clamp technique. When the peak Cl⁻ current ($I_{Cl}$) elicited by $3 \times 10^{-6}$M GABA alone was presented as 1, the augumentive $I_{Cl}$ of the test compounds in the presence of $3 \times 10^{6-}$M GABA was measured. The results were presented as relative $I_{Cl}$ values in Table 1.

TABLE 1

| Test compound (Example No.) | BZP receptor binding Ki (nM) | Relative $I_{C1}$ [1] |
| --- | --- | --- |
| 6 | 4.3 | 1.78 |
| 16 | 4.2 | 1.38 |
| 20 | 7.5 | 1.75 |

[1] $I_{C1}$ = above ca. 2: full agonist
$I_{C1}$ = ca. 1.3 to ca. 1.9: partial agonist
[Br. J. Pharmacol., vol. 98, 735–740 (1989)]

Experiment 3: Anti-conflict action

The test is carried out according to the method of Vogel et al. [Psychopharmacology, 21, 1 (1971)]. Groups of 10 to 14 male Wistar rats weighing 150–200 g are used. They are deprived of water for 72 hours before the test. The experimental apparatus is composed of a light compartment and a dark compartment equipped with a nozzle for water supply, where the rats are allowed to ambulate between the two compartments. One hour after the oral administration of the test compound, the rat is placed into the test apparatus where an electric shock is given once every 20th lick through the nozzle and grid floor. After the rat receive the first electric shock, the number of shocks are recorded during the subsequent 3 minutes test period. The minimum effective dose (MED) is defined as the lowest dose producing a statistically significant difference from methyl cellulose-treated group by t-test.

Experiment 4: Muscle-relaxant effect

Groups of 10 male ddY mice are used. The mice are gently placed on the rod (2.8 cm in diameter rotating at 11 r.p.m. ) one hour after the oral administration of the test compound. The $ED_{50}$ value is calculated by the probit method as the dose which cause 50% of the animals to drop off the rotarod within 1 minute.

Experiment 5: Potentiation of narcotic effect

Groups of 7 male mice are administered orally with test compound and one hour later administered intraperitoneally with subnarcotic dose of hexobarbital at 40 mg/kg. The loss of righting reflex is determined at 15 and 30 minutes after hexobarbital treatment. The $ED_{50}$ (mg/kg) is calculated by the probit method as the dose which cause a loss of righting reflex for more than 3 seconds in 50% of the animals.

Experiment 6: Acute toxicity

Groups of 5 male ddY mice were used. The mice were administered with 300 mg/kg of the compound of Example 16 intraperitoneally, but all mice survived for 5 days after the administration. Similarly, the mice were orally administered with 1000 mg/kg of the compound, but they survived for 5 days after the administration.

As apparent from the various pharmacological studies including the above experiments, the compounds of formula (I) of the present invention possessed high affinity for BZP receptors, and exhibited antagonistic action against chemical convulsion, such as bicuculline.

Especially, since the compounds of the present invention had high affinity for type I receptor of BZP receptors and further showed the property as a BZP partial agonist in the electrophysiological experiment, they are fully dissociated from the side effects such as muscle-relaxation, sedation, interaction with alcohol/barbiturates etc. and are useful as an anxioselective anxiolytic agent. Furthermore, it is recognized that the compounds of the present invention show potent anxiolytic activity in in vivo experiments of the various animal models of anxiety such as water-lick method by Vogel et al, elevated plus maze method [Costall et al. (Br. J. Pharmacol., 96, 312 (1989)); Meert et al. (Drug. Develop. Res., 18, 119 (1989)); Singh et al. (Br. J. Pharmacol., 104, 239 (1991))], social interaction method [File et al. (J. Neurosci. Methods, 2, 219 (1980))] or light and dark compartments method [Jones et al. (Br. J. Pharmacol., 93, 985 (1988))] and that they are largely separated from the side effects (muscle-relaxation, potentiation of narcosism). Consequently, the compounds of the present invention can be used as anxiolytic agent with high safety. When the compounds of formula (I) of the present invention are used as pharmaceuticals, a therapeutically effective amount of the compounds and adequate pharmaceutically acceptable additives such as excipient, carrier or diluent are mixed to be formulated into a form such as tablets, capsules, granules, syrups, injectable solutions, suppositories or dispersible powders and are administered in the form mentioned above. The dosage may generally range about 5 to about 500 mg per day for an adult in a single dose or divided doses in the case of oral administration.

DESCRIPTION OF THE PREFERRED EMBODIMENTS

The present invention will be explained in more detail by the following Reference examples and Examples, but these examples are not to be construed as limiting the present invention.

REFERENCE EXAMPLE 1

A mixture of 4.7 g of N-methylformanilide in 3.3 ml of phosphrus oxychloride was stirred at room temperature for an hour and 5.4 g of 2-(4-methylphenyl)-2,5,6,7-tetrahydro-3H-thieno-[2',3':6,7]cyclohepta[1,2-c]pyridazin-3-one was added thereto. After stirring at room temperature for 2 hours, the mixture was poured into ice-cold water and extracted with chloroform. The extract was washed with water, dried over anhydrous magnesium sulfate and concentrated in vacuo. The residue was chromatographed on a silica gel column using a mixed solvent of hexane and ethyl acetate (2:1) as an eluent. The solid was recrystallized from a mixed solvent of ethanol and ethyl acetate to give 3.5 g of 9-formyl-2-(4-methylphenyl)-2,5,6,7-tetrahydro-3H-thieno-[2',3':6,7]cyclohepta[1,2-c]pyridazin-3-one as a pale brown powder, melting at 127°–129° C.

REFERENCE EXAMPLE 2

The reaction and procedure were conducted in a similar manner as in Reference example 1 using 2-(4-methoxyphenyl)-2,5,6,7-tetrahydro-3H-thieno-[2',3':6,7]cyclohepta[1,2-c]pyridazin-3-one instead of 2-(4-methylphenyl)- 2,5,6,7-tetrahydro-3H-thieno-[2',3':6,7]cyclohepta[1,2-c]pyridazin-3-one to give 9-formyl-2-(4.-methoxyphenyl)-2,5,6,7-tetrahydro-3H-thieno-[2',3':6,7]cyclohepta[1,2-c]pyridazin-3-one as a pale yellow powder, melting at 131°–132° C.

REFERENCE EXAMPLE 3

The reaction and procedure were conducted in a similar manner as in Reference example 1 using 2-(4-chlorophenyl)-5,6-dihydrothieno-[2,3-h]cinnolin-3(2H)-one instead of 2-(4-methylphenyl)-2,5,6,7-tetrahydro-3H-thieno-[2',3':6,7]cyclohepta[1,2-c]pyridazin-3-one to give 2-(4-chlorophenyl)-8-formyl-5,6-dihydrothieno-[2,3-h]cinnolin-3(2H)-one as a pale yellow powder, melting at 242°–244° C.

EXAMPLE 1

To a suspension of 1.4 g of 9-formyl-2-(4-methylphenyl)-2,5,6,7-tetrahydro-3H-thieno-[2',3':6,7]cyclohepta[1,2-c]pyridazin-3-one in methanol was added 1.0 g of sodium borohydride under ice-cooling. After stirring for an hour, the mixture was poured into diluted hydrochloric acid and extracted with chloroform. The extract was washed with brine, dried over anhydrous magnesium sulfate and concentrated in vacuo. The residue was chromatographed on a silica gel column using chloroform as an eluent. The solid was recrystallized from a mixed solvent of ethanol and isopropyl ether to give 1.0 g of 9-hydroxymethyl-2-(4-methylphenyl)-2,5,6,7-tetrahydro-3H-thieno-[2',3':6,7]cyclohepta[1,2-c]pyridazin-3-one as a white powder, melting at 158°–159° C.

EXAMPLE 2

The reaction and procedure were conducted in a similar manner as in Example 1 using 9-formyl-2-(4-methoxyphenyl) -2,5,6,7-tetrahydro-3H-thieno-[2',3':6,7]cyclohepta[1,2-c]pyridazin-3-one instead of 9-formyl-2-(4-methylphenyl)-2,5,6,7-tetrahydro-3H-thieno-[2',3':6,7]cyclohepta[1,2-c]pyridazin-3-one to give 9-hydroxymethyl-2-(4-methoxyphenyl)-2,5,6,7-tetrahydro-3H-thieno-[2',3':6,7] cyclohepta[1,2-c]pyridazin-3-one as a pale yellow powder, melting at 130°–131° C.

EXAMPLE 3

The reaction and procedure were conducted in a similar manner as in Example 1 using 2-(4-chlorophenyl)-9-formyl-2,5,6,7-tetrahydro-3H-thieno-[2',3':6,7]cyclohepta[1,2-c]pyridazin-3-one instead of 9-formyl-2-(4-methylphenyl)-2,5,6,7-tetrahydro-3H-thieno-[2',3':6,7]cyclohepta[1,2-c]pyridazin-3-one to give 2-(4-chlorophenyl)-9-hydroxymethyl-2,5,6,7-tetrahydro-3H-thieno-[2',3':6,7]cyclohepta[1,2-c]pyridazin-3-one as a pale brown powder, melting at 118°–121° C.

EXAMPLE 4

The reaction and procedure were conducted in a similar manner as in Example 1 using 2-(4-chlorophenyl)-8-formyl-5,6-dihydrothieno-[2,3-h]cinnolin-3(2H)-one instead of 9-formyl-2-(4-methylphenyl)-2,5,6,7-tetrahydro-3H-thieno-[2',3':6,7]cyclohepta[1,2-c]pyridazin-3-one to give 2-(4-chlorophenyl)-8-hydroxymethyl-5,6dihydrothieno-[2,3-h]cinnolin-3(2H)-one as a pale brown powder, melting at 195°–197° C.

EXAMPLE 5

A mixture of 1.9 g of N-methylformanilide in 1.3 ml of phosphrus oxychloride was stirred at room temperature for an hour and 2.0 g of 2-(4-methylphenyl)-5,6-dihydrothieno-[2,3-h]cinnolin-3(2H)-one was added thereto. After stirring at room temperature for 10 hours, the mixture was poured into ice-cold water and extracted with chloroform. The extract was washed with water, dried over anhydrous magnesium sulfate and concentrated in vacuo. The residue was dissolved in methanol and 1.0 g of sodium borohydride was added thereto under ice-cooling. After stirring for an hour, the mixture was poured into diluted hydrochloric acid and extracted with chloroform. The extract was washed with brine, dried over anhydrous magnesium sulfate and concentrated in vacuo. The residue was chromatographed on a silica gel column using a mixed solvent of hexane and ethyl acetate (2:1) as an eluent. The solid was recrystallized from a mixed solvent of isopropyl alcohol and isopropyl ether to give 0.2 g of 8-hydroxymethyl-2-(4-methylphenyl)-5,6-dihydrothieno-[2,3-h]cinnolin3(2H)-one as a brown powder, melting at 166°–169° C.

EXAMPLE 6

To a suspension of 0.75 g of 9-hydroxymethyl-2-(4-methylphenyl)2,5,6,7-tetrahydro-3H-thieno-[2',3':6,7]cyclohepta[1,2-c]pyridazin-3-one in methanol was added 0.1 ml of conc. sulfuric acid at room temperature and the mixture was refluxed under heating for 3 hours. The mixture was poured into aqueous sodium hydrogen carbonate solution and extraced with chloroform. The extract was washed with brine, dried over magnesium sulfate and concentrated in vacuo. The residue was chromatographed on a silica gel column using chloroform as an eluent. The solid was recrystallized from a mixed solvent of ethanol and isopropyl ether to give 0.7 g of 9-methoxymethyl-2-(4-methylphenyl)-2,5,6,7-tetrahydro-3H-thieno-[2',3':6,7]cyclohepta[1,2-c]pyridazin-3-one as a white powder, melting at 109°–110° C.

EXAMPLE 7

The reaction and procedure were conducted in a similar manner as in Example 6 using 9-hydroxymethyl-2-(4-methoxyphenyl)-2,5,6,7-tetrahydro-3H-thieno-[2',3':6,7]cyclohepta[1,2-c]pyridazin-3-one instead of 9-hydroxymethyl-2-(4-methylphenyl)-2,5,6,7-tetrahydro-3H-thieno-[2',3':6,7]cyclohepta[1,2-c]pyridazin-3-one to give 9-methoxymethyl-2-(4-methoxyphenyl)-2,5,6,7-tetrahydro-3H-thieno-[2',3':6,7]cyclohepta[1,2-c]- pyridazin-3-one as a white powder, melting at 115°–117°C.

EXAMPLE 8

The reaction and procedure were conducted in a similar manner as in Example 6 using 2-(4-chlorophenyl)-9-hydroxymethyl-2,5,6,7-tetrahydro-3H-thieno-[2',3':6,7]cyclohepta[1,2-c]pyridazin-3-one instead of 9-hydroxymethyl-2-(,4-methylphenyl)-2,5,6,7-tetrahydro-3H-thieno-[2',3':6,7]cyclohepta[1,2-c]pyridazin-3-one to give 2-(4-chlorophenyl)-9-methoxymethyl-2,5,6,7-tetrahydro-3H-thieno-[2',3':6,7]cyclohepta[1,2-c]- pyridazin-3-one as a white powder, melting at 135°–137° C.

EXAMPLE 9

The reaction and procedure were conducted in a similar manner as in Example 6 using 2-(,4-chlorophenyl)-8-hydroxymethyl-5,6-dihydrothieno-[2,3-h]cinnolin-3(2H)-one instead of 9-hydroxymethyl-2-(4-methylphenyl)-2,5,6,7-tetrahydro-3H-thieno-[2',3':6,7]cyclohepta[1,2-c]-pyridazin-3-one to give 2-(4-chlorophenyl)-8-methoxymethyl-5,6-dihydrothieno-[2,3-h]cinnolin-3(2H)-one as a pale yellow powder, melting at 159°–160° C.

EXAMPLE 10

The reaction and procedure were conducted in a similar manner as in Example 6 using 8-hydroxymethyl-2-(4-methylphenyl)-5,6-dihydrothieno-[2,3-h]cinnolin-3(2H)-one instead of 9-hydroxymethyl-2-(4-methylphenyl)- 2,5,6,7-tetrahydro-3H-thieno-[2',3':6,7]cyclohepta[1,2-c]-pyridazin-3-one to give 8-methoxymethyl-2-(4-methylphenyl)-5,6-dihydrothieno-[2,3-h]cinnolin-3(2H)-one as a pale brown powder, melting at 132°–133° C.

EXAMPLE 11

The reaction and procedure were conducted in a similar manner as in Example 6 using ethanol instead of methanol to give 9-ethoxymethyl-2-(4-methylphenyl)-2,5,6,7-tetrahydro-3H-thieno-[2',3':6,7]cyclohepta[1,2-c]-pyridazin-3-one as a white powder, melting at 92°–93° C.

EXAMPLE 12

To a suspension of 5.7 g of aluminum chloride in 100 ml of methylene chloride was added 2.0 ml of acetyl chloride under ice-cooling and the mixture was stirred at room temperature for 10 minutes. 4.5 g of 2-(4-chlorophenyl)-4,4a,5,6-tetrahydrothieno-[2,3-h]cinnolin-3(2H)-one was added under ice-cooling, and the mixture was refluxed for 2 hours. After cooling, the mixture was poured into ice-cold water and extracted with chloroform. The extract was washed with water, dried over anhydrous magnesium sulfate and the solvent was concentrated in vacuo. The resulting crystal was recrystallized from a mixed solvent of chloroform and ethanol to give 4.7 g of 8-acetyl-2-(4-chlorophenyl)-4,4a,5,6tetrahydrothieno-[2,3-h]cinnolin-3(2H)-one as a white crystal, melting at 155°–157° C.

EXAMPLE 13

The reaction and procedure were conducted in a similar manner as in Example 12 using propionyl chloride instead of acetyl chloride to give 2-(4-chlorophenyl)-4,4a,5,6-tetrahydro-8-propionylthieno-[2,3-h ]cinnolin-3(2H)-one as a white crystal, melting at 135°–138° C.

EXAMPLE 14

The reaction and procedure were conducted in a similar manner as in Example 12 using butyryl chloride instead of acetyl chloride to give 8-butyryl-2-(4-chlorophenyl)-4,4a,5,6-tetrahydrothieno[2,3-h]cinnolin-3(2H)-one as a white crystal, melting at 157°–159° C.

EXAMPLE 15

The reaction and procedure were conducted in a similar manner as in Example 12 using 4,4a,5,6-tetrahydro-2-(4-methylphenyl)thieno-[2,3-h]cinnolin-3(2H)-one instead of 2-(4-chlorophenyl)-4,4a,5,6-tetrahydrothieno-[2,3-h]cinnolin-3(2H)-one to give 8-acetyl-4,4a, 5,6-tetrahydro-2-(4methylphenyl)thieno[2,3-h]cinnolin-3(2H)-one as a white crystal, melting at 191°–193° C.

EXAMPLE 16

The reaction and procedure were conducted in a similar manner as in Example 12 using 2-(4-chlorophenyl)-2,4,4a,5,6,7-hexahydro-3H-thieno-[2',3':6,7]cyclohepta[1,2-c]pyridazin-3-one instead of 2-(4-chlorophenyl)-4,4a,5,6-tetrahydrothieno-[2,3-h]cinnolin-3(2H)-one to give 9-acetyl-2-(4-chlorophenyl)-2,4,4a, 5,6,7-hexahydro-3H-thieno-[2',3':6,7]cyclohepta[1,2-c]pyridazin-3-one as a white crystal, melting at 128°–130° C.

EXAMPLE 17

To a solution of 1.2 g of 9-acetyl-2-(4-chlorophenyl)-2,4,4a,5,6,7-hexahydro-3H-thieno-[2',3':6,7]cyclohepta[1,2-c]pyridazin-3-one in 15% hydrogen bromide-acetic acid solution was added 0.23 ml of dimethylsulfoxide at room temperature with stirring. After stirring at the same temperature for 15 minutes, the mixture was poured into 0.5% sodium hydrogensulfite solution and extracted with chloroform. The extract was washed with water, dried over anhydrous magnesium sulfate and concentrated. The residue was chromatographed on a silica gel column using chloroform as an eluent. The resulting solid was recrystallized from ethanol to give 0.4 g of 9-acetyl-2-(4-chlorophenyl)-2,5,6,7-tetrahydro-3H-thieno-[2',3':6,7]cyclohepta[1,2-c]pyridazin-3-one as a white crystal, melting at 164°–166° C.

REFERENCE EXAMPLE 4

A mixture of 0.45 g of N-methylformanilide in 0.33 ml of phosphrus oxychloride was stirred at room temperature for an hour and 0.5 g of 2-(4 -chlorophenyl)-2,5,6,7-tetrahydro-3H-thieno-[2',3':6,7]cyclohepta[1,2-c]pyridazin-3-one was added thereto. After stirring at room temperature for 2 hours, the mixture was poured into ice-cold water and extracted with ethyl acetate. The extract was washed with water, dried over anhydrous magnesium sulfate and concentrated in vacuo. The residue was chromatographed on a silica gel (SiO$_2$:40 g) column using chloroform as an eluent. The resulting solid was recrystallized from a mixed solvent of chloroform and ethanol to give 0.25 g of 2-(4-chlorophenyl)-9-formyl-2,5,6,7-tetrahydro-3H-thieno-[2',3':6,7]-cyclohepta[1,2-c]pyridazin-3-one as a pale yellow powder, melting at 170°–172° C.

EXAMPLE 18

To a suspension of 1.3 g of 8-acetyl-4,4a, 5,6-tetrahydro-2-(4-methylphenyl)thieno-[2,3-h]cinnolin-3(2H)-one in methanol was added 300 mg of sodium borohydride under ice-cooling and the mixture was stirred for 3 hours. The mixture was concentrated in vacuo until about a half volume of the methanol was evaporated and water was added, and then extracted with chloroform. The extract was washed with brine, dried over anhydrous magnesium sulfate and concentrated in vacuo. The residue was chromatographed on a silica gel (SiO$_2$:30 g) column using a mixed solvent of chloroform and methanol (98:2) as an eluent. The resulting solid was recrystallized from a mixed solvent of ethyl acetate and hexane to give 570 mg of 8-(1-hydroxyethyl)-4,4a,5,6-tetrahydro-2-(4-methylphenyl)thieno-[2,3-h]cinnolin-3(2H)-one as a pale yellow powder, melting at 129°–145° C.

EXAMPLE 19

To a suspension of 6.4 g of aluminum chloride in methylene chloride was added 2.3 ml of acetyl chloride under ice-cooling and the mixture was stirred for 10 minutes. A solution of 4.7 g of 5,6-dihydro-2-(4-methylphenyl)thieno-[2,3-h]cinnolin-3(2H)-one in methylene chloride was added thereto, the mixture was stirred at room temperature for 30 minutes and then refluxed for an hour. The mixture was poured into ice-cold water and extracted with chloroform. The extract was washed with water, dried over anhydrous magnesium sulfate and concentrated in vacuo. The residue was chromatographed on a silica gel (SiO$_2$:100 g) column using chloroform as an eluent. The resulting solid was recrystallized from a mixed solvent of chloroform and methanol to give 3.7 g of 8-acetyl-5,6-dihydro-2-(4-methylphenyl)thieno-[2,3-h]cinnolin-3(2H)-one as a white powder, melting at 240°–242° C.

EXAMPLE 20

To a suspension of 600 mg of 8-acetyl-5,6-dihydro-2-(4-methylphenyl)thieno-[2,3-h]cinnolin-3(2H)-one in 100 ml of methanol was added 70 mg of sodium borohydride with stirring under ice-cooling. The mixture was stirred for 3 hours and poured into ice-cold water and then extracted with chloroform. The extract was washed with brine, dried over anhydrous magnesium sulfate and concentrated in vacuo.

The residue was chromatographed on a silica gel (SiO$_2$:20 g) column using a mixed solvent of chloroform and methanol (98:2) as an eluent. The resulting solid was recrystallized from a mixed solvent of ethyl acetate and hexane to give 300 mg of 8-(1-hydroxyethyl)-5,6-dihydro-2-(4-methylphenyl)thieno-[2,3-h]cinnolin-3(2H)-one as a pale yellow powder, melting at 146°–148° C.

REFERENCE EXAMPLE 5

To a suspension of 20.3 g of aluminum chloride in methylene chloride was added 8.1 ml of chloroacetyl chloride under ice-cooling. A solution of 15 g of 4,4a,5,6-tetrahydro-2-(,4-methylphenyl)thieno-[2,3-h]cinnolin-3(2H)-one in methylene chloride was added thereto. The mixture was refluxed for 8 hours, and poured into ice-cold water and then extracted with chloroform. The extract was washed with water, dried over anhydrous magnesium sulfate and concentrated in vacuo. The residue was chromatographed on a silica gel (SiO$_2$:600 g) column using chloroform as an eluent. The starting material (7.2 g) was recovered from the first fraction and the desired compound was obtained from the second fraction. The crystal was recrystallized from a mixed solvent of chloroform and ethanol to give 6.5 g of 8-chloroacetyl-4,4a,5,6-tetrahydro-2-(4-methylphenyl)thieno-[2,3-h]cinnolin-3(2H)-one as a pale yellow powder, melting at 169°–171° C.

REFERENCE EXAMPLE 6

To a suspension of 5.8 g of 8-chloroacetyl-4,4a,5,6-tetrahydro-2-(4-methylphenyl)thieno-[2,3-h]cinnolin-3(2H)-one in 100 ml of acetic acid was added 12 g of potassium acetate and the mixture was stirred for 5 hours. The mixture was poured into ice-cold water and the precipitate was collected by filtration. The filtrate was extracted with ethyl acetate. The extract was washed with brine, dried over anhydrous magnesium sulfate and concentrated in vacuo. The residue and the precipitate were combined and chromatographed on a silica gel (SiO$_2$:200 g) column using chloroform as an eluent. The resulting crystals were recrystallized from a mixed solvent of chloroform and methanol to give 4.4 g of 8-acetoxyacetyl-4,4a, 5,6-tetrahydro-2-(4-methylphenyl)thieno-[2,3-h]cinnolin-3(2H)-one as a white powder, melting at 144°–145° C.

REFERENCE EXAMPLE 7

To a solution of 3 g of 8-acetoxyacetyl-4,4a,5,6-tetrahydro-2-(4methylphenyl)thieno-[2,3-h]cinnolin-3(2H)-one in 30 ml of trifluoroacetic acid was added 2.7 ml of triethylsilane and the mixture was stirred at room temperature for 24 hours. The mixture was poured into ice-cold water, neutralized with potassium carbonate and then extracted with chloroform. The extract was washed with brine, dried over anhydrous magnesium sulfate and concentrated in vacuo. The residue was chromatographed on a silica gel (SiO$_2$:100 g) column using chloroform as an eluent. The resulting solid was recrystallized from a mixed solvent of ethyl acetate and hexane to give 2.0 g of 8-(2-acetoxyethyl)-4,4a,5,6-tetrahydro-2-(4-methylphenyl)thieno-[2,3-h]cinnolin-3(2H)-one as a white powder, melting at 73°–75° C.

EXAMPLE 21

To a suspension of 1.5 g of 8-(2-acetoxyethyl) -4,4a,5,6-tetrahydro-2-(4-methylphenyl)thieno-[2,3-h]cinnolin-3(2H)-one in 50 ml of methanol was added 5 ml of aqueous solution of 0.7 g of potassium carbonate under ice-cooling. The mixture was stirred for an hour, and poured into water and then extracted with ethyl acetate. The extract was washed with brine, dried over anhydrous magnesium sulfate and concentrated in vacuo. The resulting solid was recrystallized from a mixed solvent of chloroform and ethanol to give 1.3 g of 4,4a,5,6-tetrahydro-8-(2-hydroxy-ethyl)-2-(4-methylphenyl)thieno-[2,3-h]cinnolin-3(2H)-one as a white powder, melting at 159°–160° C.

The compounds exemplified in the following tables can be prepared in a similar manner as the above examples.

TABLE 2

| No. | R$^1$ | R$^2$ | ══bond |
|---|---|---|---|
| 22 | 8-CHCH$_3$<br>\|<br>OH | ―⟨phenyl⟩―Cl | single |
| 23 | " | " | double |
| 24 | 8―COCH$_3$ | ―⟨phenyl⟩―OCH$_3$ | single |
| 25 | " | " | double |
| 26 | 8―CH$_2$OCH$_3$ | ―⟨phenyl⟩―Br | single |
| 27 | " | " | double |
| 28 | 8―CH$_2$OH | " | single |
| 29 | " | " | double |

TABLE 3

| No. | R$^1$ | R$^2$ | ══bond |
|---|---|---|---|
| 30 | 9-CHCH$_3$<br>\|<br>OH | ―⟨phenyl⟩―Cl | single |
| 31 | " | " | double |
| 32 | 9―COCH$_3$ | ―⟨phenyl⟩―F | single |

TABLE 3-continued

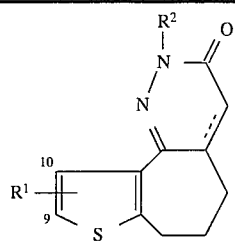

| No. | R¹ | R² | =bond |
|---|---|---|---|
| 33 | " | " | double |

TABLE 4

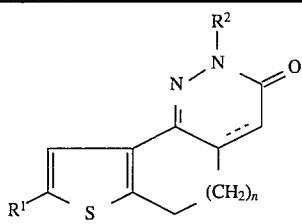

| No. | R¹ | R² | n | =bond |
|---|---|---|---|---|
| 34 | —CHCH₃<br>\|<br>OH | ⟨phenyl⟩—Cl | 1 | single |
| 35 | " | " | 1 | double |
| 36 | —COCH₃ | " | 1 | single |
| 37 | " | " | 1 | double |
| 38 | —CH₂CH₂OCH₃ | ⟨phenyl⟩—CH₃ | 1 | single |
| 39 | " | " | 1 | double |
| 40 | " | " | 2 | single |
| 41 | " | " | 2 | double |

Formulation Example

Tablets containing 10 mg of a compound of the formula (I) are prepared in accordance with the following formulation:

| | |
|---|---|
| Compound of formula (I) | 10.0 mg |
| Lactose | 58.5 mg |
| Corn starch | 25.0 mg |
| Crystalline cellulose | 20.0 mg |
| Polyvinylpyrrolidone K-30 | 2.0 mg |
| Talc | 4.0 mg |
| Magnesium stearate | 0.5 mg |
| | 120.0 mg |

The compound of the formula (I) is pulverized by an atomizer into fine powders below 10 μ in average particle diameter, which are admixed with lactose, corn starch and crystalline cellulose sufficiently in a kneading machine, and further kneaded with polyvinylpyrrolidone paste. The kneaded mixture is passed through a sieve of 200 mesh, dried at 50(3 and passed through a sieve of 24 mesh. Talc and magnesium stearate are mixed therewith and the mixture is compressed into 120.0 mg tablets with a punch of 8mm in diameter. These tablets are, if desired, subjected to sugar-coating or film-coating.

While the present invention has been adequately and sufficiently described in the foregoing specification including examples, the description can be changed or modified within the spirit and scope of this invention.

What is claimed is:

1. A fused pyridazine compound of the formula:

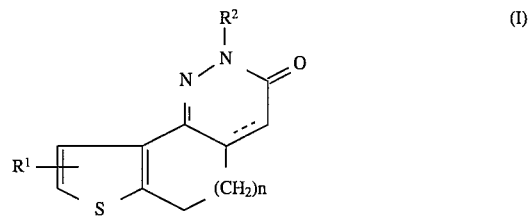

(I)

wherein:

R¹ is hydroxyalkyl having 1 to 4 carbon atoms in the alkyl moiety or alkoxyalkyl having 1 to 4 carbon atoms in each of the alkoxy and alkyl moieties;

R² is phenyl having at least one substituent selected from the group consisting of halogen, alkyl having 1 to 4 carbon atoms and alkoxy having 1 to 4 carbon atoms;

n is 1 or 2;

the bond represented by the full line and dotted line is a single bond or a double bond.

2. A fused pyridazine compound according to claim 1, which is selected from the group consisting of:

9-methoxymethyl-2-(4-methylphenyl)-2,5,6,7-tetrahydro-3H-thieno-[2',3':6,7]cyclohepta[1,2-c]pyridazin-3-one, 8-(1-hydroxyethyl)-5,6-dihydro-2-(4-methylphenyl)thieno [2,3-h]cinnolin-3(2H)-one.

3. A fused pyridazine compound according to claim 1, which is 9-methoxymethyl-2-(4-methylphenyl)-2,5,6,7-tetrahydro-3H-thieno-[2',3':6,7]cyclohepta[1,2-c]pyridazin-3-one.

4. A fused pyridazine compound according to claim 1 which is 8-(1-hydroxyethyl)-5,6-dihydro-2-(4-methylphenyl) thieno-[2,3-h ]cinnolin-3(2H)-one.

* * * * *